(12) United States Patent
Fuertes et al.

(10) Patent No.: US 8,399,601 B2
(45) Date of Patent: Mar. 19, 2013

(54) METHOD FOR PREPARING A DIALKYL CARBONATE OF DIANHYDROHEXITOL

(75) Inventors: Patrick Fuertes, Lomme (FR); Mathias Ibert, La Chapelle D'armentieres (FR); Emilie Josien, St. Venant (FR); Pietro Tundo, Mestre-venezia (IT); Fabio Arico, Padova (IT)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 13/265,235

(22) PCT Filed: Sep. 30, 2010

(86) PCT No.: PCT/FR2010/052066
§ 371 (c)(1),
(2), (4) Date: Oct. 19, 2011

(87) PCT Pub. No.: WO2011/039483
PCT Pub. Date: Apr. 7, 2011

(65) Prior Publication Data
US 2012/0041169 A1    Feb. 16, 2012

(30) Foreign Application Priority Data
Oct. 1, 2009    (FR) ..................... 09 56835

(51) Int. Cl.
*C08G 64/00*    (2006.01)
*C08G 63/02*    (2006.01)
(52) U.S. Cl. ........................ 528/352; 528/354
(58) Field of Classification Search .................. 528/352, 528/354
See application file for complete search history.

(56) References Cited

U.S. PATENT DOCUMENTS
2004/0241553 A1    12/2004 Abe et al.

FOREIGN PATENT DOCUMENTS
EP    2 033 981 A1    3/2009
JP    6 261774 A    9/1994

OTHER PUBLICATIONS

Saber Chatti et al. "Cyclic and Noncyclic Polycarbonates of Isosorbide (1,4:3,6-dianhydro-D-glucitol)", in Macromolecules, 2006, 9061-9070, Received Mar. 17, 2006; Revised Manuscript Received Oct. 30,2006.
Okada, Masahiko et al: "Biodegradable polymers based on renewable resources. VI. Synthesis and biodegradability of poly(ester carbonate)s containing 1,4:3,6-dianhydro-D-glucitol and sebacic acid units", 2002, Journal of Applied Polymer Science , 86( 4), 872-880 CODEN: JAPNAB; ISSN: 0021-8995, XP002582390, p. 878.
International Search Report, dated Dec. 15, 2010, from corresponding PCT application.

*Primary Examiner* — Terressa Boykin
(74) *Attorney, Agent, or Firm* — Young & Thompson

(57) ABSTRACT

A method for preparing dialkyl carbonates of dianhydrohexitol, includes the following steps: (a) preparing an initial reaction mixture containing at least one dianhydrohexitol, at least two mole equivalents of a dialkyl carbonate of formula and a transesterification catalyst; (b) heating the reaction mixture to a temperature greater than or equal to the boiling temperature of the formed alcohol, or of the azeotrope thereof, in a reaction chamber preferably provided with a rectification column including a sufficient number of theoretical distillation plates to separate the resulting alcohol from the reaction mixture. Certain dialkyl carbonates of dianhydrohexitols produced by the method and the use thereof for synthesizing synthetic polymers are also described.

20 Claims, No Drawings

METHOD FOR PREPARING A DIALKYL CARBONATE OF DIANHYDROHEXITOL

FIELD OF THE INVENTION

The present invention relates to a novel process for the preparation of 1,4:3,6-dianhydrohexitol di(alkyl carbonate)s, to some novel dialkyl carbonates obtained by this process and to the use of the dianhydrohexitol di(alkyl carbonate)s in the preparation of synthetic polymers, in particular as (co)monomers for the synthesis of polycarbonates and polycarbamates, or as chain-extending agent for increasing the molecular weight of polymers comprising reactive end groups capable of reacting with carbonate functional groups.

BACKGROUND OF THE INVENTION

Polycarbonates are amorphous thermoplastic materials conventionally obtained by polycondensation of diols and diphenyl carbonate, phosgene or diphosgene.

The toxicity of the phosgene, of the diphosgene or of the phenol inevitably formed in the event of the use of diphenyl carbonate constitutes a major disadvantage in the synthesis of polycarbonates.

The development of polymeric materials resulting from biological resources renewable in the short term has become an ecological and economic imperative in the face of the exhaustion and of the rise in the cost of fossil resources, such as oil.

In this context, the use of dianhydrohexitols, resulting from plant (poly)saccharides, as dihydroxylated monomers in polycondensation reactions appears to be a promising approach to replacing monomers of petrochemical origin.

The preparation of isosorbide-based polycarbonates has been described in patent application EP 2 033 981. This document describes the polycondensation of a mixture of isosorbide, of at least one second alicyclic diol and of diphenyl carbonate. The process exhibited a disadvantage, already mentioned above, of generating phenol as byproduct of the polymerization reaction.

The paper by Saber Chatti, entitled "Cyclic and Noncyclic Polycarbonates of Isosorbide (1,4:3,6-dianhydro-D-glucitol)", in Macromolecules, 2006, 9061-9070, envisages various routes for the synthesis of isosorbide-based polycondensates. A first synthetic route, consisting in heating isosorbide in the presence of four molar equivalents of dimethyl or diethyl carbonate and in the presence of a catalyst chosen from potassium tert-butoxide (KOtBu), tin dioctanoate (SnOct$_2$) and titanium tetrabutoxide (Ti(OBu)$_4$), at temperatures of between 100° C. and 200° C., is described as not making it possible to obtain isosorbide polycarbonates. According to the authors of this paper, unreacted isosorbide is recovered after reacting at 200° C. for more than two hours. This failure was confirmed by the Applicant Company, which observed that heating a mixture of isosorbide and of dimethyl carbonate in the presence of potassium tert-butoxide, tin dioctanoate or titanium tetrabutoxide resulted in mixtures comprising a high proportion of isosorbide alkyl ethers and a low proportion, indeed even zero proportion, of isosorbide methyl carbonate. These three catalysts thus prove to also or solely be etherification catalysts and not solely transesterification catalysts, as desired in the present invention. They do not make it possible to selectively form dianhydrohexitol di(alkyl carbonate)s and thus, indirectly, cannot be used for the purpose of the preparation of polymers (polycarbonates).

The paper by Saber Chatti describes two other synthetic routes which, however, both suffer from the disadvantage of requiring the use of toxic, indeed even highly toxic, reactants or solvents (phosgene, diphosgene, pyridine, isosorbide bischloroformate).

The preparation of dianhydrohexitol di(alkyl carbonate)s has also been described in patent application US 2004/241553. This document describes a process for the manufacture of dianhydrohexitol di(alkyl carbonate) by reaction of a dianhydrohexitol and of a chloroformate ester. This manufacturing process exhibits the major disadvantage of involving a toxic compound, i.e., a chloroformate ester.

The document JP 6-261774 also describes a process for the preparation of dianhydrohexitol di(alkyl carbonate) (example 5). However, this preparation process again here involves toxic chloroformic entities.

SUMMARY OF THE INVENTION

The present invention is based on the discovery that some specially selected catalysts, furthermore used under specific reaction conditions, make it possible to obtain dianhydrohexitol di(alkyl carbonate)s, some of which have never been isolated hitherto, with virtually quantitative yields and in the absence of the use of toxic reactants.

The Applicant Company means here, by "virtually quantitative", dianhydrohexitol di(alkyl carbonate) yields of greater than 70%, preferably of greater than or equal to 75% and more preferably still of greater than or equal to 80%, or yields of dianhydrohexitol di(alkyl carbonate) and of oligomers of greater than 90%. The fact of having available, by virtue of the novel process of the invention, dianhydrohexitol di(alkyl carbonate)s in the pure or virtually pure form makes it possible to prepare polycarbonates based on dianhydrohexitols, in particular based on isosorbide, without the use of toxic reactants. The dianhydrohexitol di(ethyl carbonate)s of the present invention even make possible the synthesis of polycarbonates or polycarbamates without any emission of toxic byproducts, such as phenol or, to a lesser extent, methanol.

A subject matter of the present invention is consequently a process for the preparation of dianhydrohexitol di(alkyl carbonate)s of formula (I)

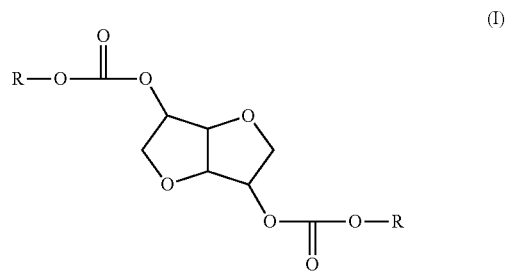

where each R independently represents a linear or branched alkyl group, preferably a $C_{1-6}$ alkyl group, in particular a methyl or ethyl group, said process comprising, in sequence, the following steps:
(a) preparation of a starting reaction mixture comprising
at least one dianhydrohexitol,
at least 2 molar equivalents, with respect to the amount of dianhydrohexitol present, of at least one dialkyl carbonate of formula R—O—C(=O)—O—R where R has the meaning indicated above, and
a transesterification catalyst, (b) heating the reaction mixture up to a temperature of greater than or equal to the boiling point of the alcohol R—OH formed by the transesterification reaction or greater than or equal to the boiling point of the azeotropic mixture which the alcohol R—OH obtained forms with another of the components present in the reaction mixture and at most equal to the boiling point of the reaction mixture, in a reactor preferably equipped with a rectification column comprising a number of theoretical distillation plates sufficient to separate, from the reaction mixture, the alcohol obtained or the azeotrope which it forms with another of the components present in the reaction mixture.

The term "1,4:3,6-dianhydrohexitol" or "dianhydrohexitol" used in the present invention encompasses isosorbide (obtained by dehydration of D-glucitol), isomannide (obtained by dehydration of D-mannitol) and isoidide (obtained by dehydration of D-iditol).

The reaction mixture prepared in step (a) can comprise one or more dianhydrohexitols but preferably comprises just one dianhydrohexitol, in particular isosorbide, available in a larger amount and at a lower cost than the other two stereoisomers.

DETAILED DESCRIPTION OF THE INVENTION

The reaction at the heart of the present invention is a transesterification reaction. It will be easily understood that, in order to result in a satisfactory fraction of difunctional derivatives, that is to say of dianhydrohexitol molecules with the two hydroxyl functional groups having been converted to alkyl carbonate R—O—(C=O)—O— functional groups, it is necessary to introduce, into the starting reaction medium, at least as many moles of dialkyl carbonate as of hydroxyl functional groups carried by the dianhydrohexitol, in other words twice as many moles of dialkyl carbonate as of moles of dianhydrohexitol.

The use of a 2:1 (dialkyl carbonate:dianhydrohexitol) molar ratio is, however, not generally optimal. This is because the dianhydrohexitol mono(alkyl carbonate) and the dianhydrohexitol di(alkyl carbonate) formed during the reaction can react with still unreacted dianhydrohexitol, which results in the formation of dimers or oligomers. This formation of dimers or oligomers can be effectively inhibited by the use of a large excess of dialkyl carbonate. The applicational examples below specifically show that, the greater the excess of diethyl carbonate or dimethyl carbonate, the lower the fraction of oligomers. A molar excess of greater than 40 makes it possible to limit the oligomer fraction to approximately 5%, preferably to approximately 1%.

The use of a very large excess of dialkyl carbonate is not however, without disadvantages. This is because it always involves an undesirable increase in the production plant. Furthermore, the greater the excess of diethyl carbonate used at the start, the more energy would have to be employed in order to remove, at the end of the transesterification reaction, this reactant from the product obtained by evaporation. It is consequently advisable to find, for each case, a compromise between an optimal content of dianhydrohexitol di(alkyl carbonate), which requires a large excess of dialkyl carbonate, and a reduction, always desirable, in the production costs.

The starting reaction mixture prepared in step (a) consequently advantageously comprises from 2.1 to 100 molar equivalents, preferably from 5 to 60 molar equivalents and in particular from 10 to 40 molar equivalents of dialkyl carbonate, with respect to the amount of dianhydrohexitol.

When, as is the case with methanol, the alcohol generated by the transesterification reaction forms an azeotropic mixture with the starting dimethyl carbonate, evaporation of this mixture "consumes" reactant. It is obvious that, in such a case, the minimum number of dialkyl carbonate equivalents is greater than the theoretical value of 2. Of course, this minimum number will depend on the proportions of the azeotropic mixture and will increase as the fraction of dialkyl carbonate in the azeotropic mixture increases. Thus, for the MeOH/DMC (70/30) azeotropic mixture, the minimum number of DMC equivalents which it is necessary to introduce into the starting reaction mixture is equal to 2.9.

The transesterification catalyst used in the process of the present invention is preferably chosen from one or more of the following:
  acid catalysts,
  alkali metal and alkaline earth metal carbonates and hydrogenocarbonates,
  alkali metal and alkaline earth metal hydroxides,
  alkali metal and alkaline earth metal phosphates, hydrogenophosphates and dihydrogenophosphates,
  ammonium salts chosen from ammonium carbonates, hydrogenocarbonates, hydroxides, phosphates, hydrogenophosphates and dihydrogenophosphates, and
  amines, in particular aromatic amines and alkyl-amines.

The ammonium salts in question can be primary, secondary, tertiary or quaternary ammonium salts.

The amine can be primary, secondary or tertiary, in particular secondary or tertiary.

The starting reaction mixture prepared in step (a) preferably comprises from 0.1 to 10 molar equivalents, in particular from 1 to 5 molar equivalents and very particularly from 1 to 3 molar equivalents of transesterification catalyst, with respect to the amount of dianhydrohexitol.

Mention may in particular be made, as transesterification catalyst, of sulfuric acid, paratoluenesulfonic acid, phosphoric acid, potassium carbonate, sodium carbonate, barium carbonate, cesium carbonate, potassium hydrogenocarbonate, sodium hydrogenocarbonate, lithium hydroxide, potassium hydroxide, sodium hydroxide, calcium hydroxide, hydrotalcites, sodium phosphate, potassium phosphate, pyridine, triethylamine and diisopropylamine.

More preferably still, the transesterification catalyst used in the process of the present invention is chosen from one or more of the following catalysts, exclusively specific to the transesterification reaction according to the invention: potassium carbonate, potassium hydroxide and lithium hydroxide.

These catalysts also exhibit the advantage of being insoluble in the reaction medium and of carrying out a heterogeneous-phase catalysis. They can thus be recovered by a simple filtration process and are consequently easy to recycle.

The starting reaction mixture can optionally comprise an organic solvent, for example an organic solvent which forms an azeotropic mixture with the alcohol R—OH, for example methanol or ethanol, formed in the reaction. In a preferred embodiment of the process of the invention, the starting reaction mixture does not, however, comprise solvents or components other than those mentioned above and is preferably composed of at least one 1,4:3,6-dianhydrohexitol, of a dialkyl carbonate and of the transesterification catalyst.

The reaction mixture is subsequently introduced into a reactor equipped with a stirring system, optionally with a rectification column and with a heating system and is heated to a temperature which is
  either greater than or equal to the boiling point of the alcohol R—OH formed by the transesterification reaction, or greater than or equal to the boiling point of the azeotrope which the alcohol R—OH forms with a component of the reaction medium, such as dialkyl carbonate or an added solvent.

The "boiling point" is, of course, that of the solvent or azeotrope at the pressure of the plant.

"Heating temperature" is understood here to mean the temperature measured by a temperature sensor in the reaction mixture. The transesterification reaction becomes faster as the heating temperature increases. However, it is, of course, impossible to heat the reaction mixture above the boiling point of the reaction mixture. It is particularly advantageous to carry out the transesterification reaction at a temperature equal to the boiling point of the reaction medium or lower than this temperature by at the very most a few degrees, for example lower than this temperature by at most 2° C.

It can be advantageous to increase the operating pressure of the system to a value greater than atmospheric pressure. This is because this might improve the reaction rate (by virtue of the increase in the boiling point) or increase the temperature difference between the alcohol or the azeotrope formed and the starting dialkyl carbonate, which would make it possible to simplify the separation by rectification and to reduce the number of theoretical plates of the rectification column.

It is possible, for example, to envisage operating at an absolute pressure between 0 and 20 bar.

When a dianhydrohexitol is reacted with dimethyl carbonate (DMC), the methanol formed forms, with the DMC, an azeotropic mixture having a boiling point equal to 62.7° C. The boiling point of DMC is equal to 90° C. Thus, when the process according to the invention is carried out with DMC, the heating temperature is between approximately 68° C. and 95° C., preferably between 85° C. and 90° C.

Ethanol (boiling point 78.3° C.), in contrast to methanol, does not form an azeotropic mixture with diethyl carbonate (DEC). Consequently, when the process according to the invention is carried out starting from DEC, the heating temperature is between approximately 83° C. and 130° C., preferably between 121 and 126° C.

In order to optimize the management of the process of the invention, it is useful to monitor the degree of progression of the reaction and to stop the heating as soon as the degree of progression is reached. The process according to the invention consequently additionally comprises the monitoring of the progression of the reaction. It is possible, for example, to monitor the amount of alcohol formed or else to keep an eye on the temperature of the vapors at the rectification column top. When the latter rapidly increases from the boiling point of the alcohol or of the azeotropic mixture comprising the alcohol to the boiling point of the dialkyl carbonate, this is the sign that the reaction is complete, generally following the consumption of all of the hydroxyl groups of the dianhydrohexitol.

The degree of progression of the esterification reaction employed in the present invention is defined by the following formula:

$$\text{Degree of progression (in \%)} = \frac{(Ni - Nt)}{Ni} \times 100$$

where
Nt=number of dianhydrohexitol hydroxyl functional groups remaining in the reaction medium at time t, and
Ni=initial number of dianhydrohexitol hydroxyl functional groups.

The heating of the reaction mixture (in step (b)) is advantageously continued up to a degree of progression of the reaction of at least 95%, preferably at least 98% and ideally equal to 100% is achieved.

It is important to note that a degree of progression equal to 100% does not mean the reaction mixture comprises only dianhydrohexitol di(alkyl carbonate). This is because, in particular when a relatively low dialkyl carbonate/dianhydrohexitol molar ratio is used, for example of less than or equal to 20 or 10, the reaction mixture comprises a certain fraction of oligomers (oligocarbonates). These oligomers do not necessarily have to be separated from the main reaction product targeted, which is dianhydrohexitol di(alkyl carbonate). This is because, for some applications, for example in the synthesis of polycarbonates or other synthetic polymers, the oligomers can perform a function equivalent to that of a dianhydrohexitol di(alkyl carbonate).

The process according to the invention preferably additionally comprises at least one step of separation of the dianhydrohexitol di(alkyl carbonate) obtained from a portion or all of the other components of the reaction mixture.

In the case of the use of a solid catalyst which is insoluble in the reaction medium, a first separation step is generally the filtration of the reaction medium, intended to remove and recycle the solid catalyst in suspension in said medium.

The reaction mixture, freed from the particles of catalyst, is subsequently subjected to an evaporation, preferably under vacuum, of the unreacted dialkyl carbonate. After evaporation of the dialkyl carbonate, either a solid product is obtained, which product can be recrystallized one or more times from an appropriate solvent. This is the case with isosorbide di(methyl carbonate), isomannide di(methyl carbonate) and isoidide di(methyl carbonate), which can be recrystallized, for example, from isopropanol.

When, as is the case with the di(ethyl carbonate) derivatives, the reaction product is liquid after evaporation of the dialkyl carbonate, it can be separated from the oligomers or mono(ethyl carbonate) derivatives by distillation.

According to a preferred embodiment of the present invention, the separation of the anhydrohexitol di(alkyl carbonate) from the oligomers can be carried out on a wiped-film evaporator of short-path configuration. The anhydrohexitol di(alkyl carbonate) is evaporated, whereas the oligomers are recovered in the unevaporated residue.

Thus, a subject matter of the present invention is advantageously a process for the preparation of dianhydrohexitol di(alkyl carbonate)s, wherein it additionally comprises a step (c) of concentration of the dianhydrohexitol di(alkyl carbonate)(s) obtained in step (b) by evaporation of the dialkyl carbonate which has not reacted during said step (b).

The present invention also relates to a process for the preparation of dianhydrohexitol di(alkyl carbonate)s, wherein it additionally comprises a step (d) of purification of the dianhydrohexitol di(alkyl carbonate)(s) concentrated in step (c).

According to a specific embodiment of the present invention, the oligomer-rich residue can advantageously be recycled to the reaction mixture. Thus, for example, said residue is reintroduced into the reactor in the presence of a minimum amount of alkanol. The Applicant Company has demonstrated, under these specific conditions, the reversibility of the transesterification reaction according to the invention. Such an addition of the oligomer-rich residue at the top of the reactor brings about the production of dianhydrohexitol and of dialkyl carbonate, so that the conditions appropriate for the reaction for the preparation of dianhydrohexitol di(alkyl carbonate) according to the invention are again combined.

Thus, the present invention advantageously relates to a process for the preparation of dianhydrohexitol di(alkyl carbonate)s, wherein the residue resulting from the purification step (d) is recycled to the reaction mixture of step (a).

Although the process according to the invention can be carried out in principle without distinction and with an equal chance of success with the three dianhydrohexitols mentioned in the introduction, preference is given, among these, for reasons of availability and of cost, to isosorbide.

The choice will preferably be made, as dialkyl carbonate, of diethyl carbonate.

To the knowledge of the Applicant Company, only isosorbide di(methyl carbonate) has to date been produced and isolated (JP 6-261774, example 5).

In contrast, dianhydrohexitol di(ethyl carbonate)s, namely isosorbide di(ethyl carbonate), isomannide di(ethyl carbonate) and isoidide di(ethyl carbonate), and also isoidide di(methyl carbonate) and isomannide di(methyl carbonate), have not to date been isolated and consequently constitute another subject matter of the invention. Among these novel compounds, dianhydrohexitol di(ethyl carbonate)s and in particular isosorbide di(ethyl carbonate) are regarded as particularly advantageous as not only can their preparation according to the invention be carried out in the absence of any toxic volatile organic compound but the use of these dianhydrohexitol derivatives in the synthesis of polymers exhibits the advantage of in principle releasing only ethanol, that is to say an organic compound regarded as nontoxic.

The alternative form of the process according to the invention resulting in the synthesis of dianhydrohexitol di(ethyl carbonate)s thus makes it possible, for the first time, to envisage the synthesis of isosorbide-based polycarbonates or more generally dianhydrohexitol-based polycarbonates without the use or the formation of any toxic compound, which is a considerable advance in comparison with the processes provided to date.

The dianhydrohexitol di(alkyl carbonate)s prepared according to the present invention in addition make it possible to synthesize alternating dianhydrohexitol-based copolymers. Such a synthesis has not been possible to date. This is because the synthesis of dianhydrohexitol-based copolymers described in EP 2 033 981 comprises the reaction of a mixture of dianhydrohexitol, of a second alicyclic dihydroxylated compound and of a dicarbonate in the presence of a transesterification catalyst. However, this synthesis results in the production of random copolymers and not of alternating copolymers having a homogeneous distribution of the comonomer units along the chain.

Consequently, another subject matter of the present invention is the use of one or more of the dianhydrohexitol di(alkyl carbonate)s prepared according to the process of the invention as monomers or comonomers in the preparation of polycarbonates, of polycarbamates or of polythiocarbonates, preferably in the preparation of alternating polycarbonates or polycarbamates.

Another subject matter of the present invention is the use of one of the compounds according to the invention or of a compound capable of being obtained by the process according to the invention as chain-extending agent, bridging agent, grafting agent and crosslinking agent for polymers carrying side or end functional groups having a labile hydrogen capable of reacting with a carbonate functional group, that is to say hydroxyl, amine, thiol, ester or oxazoline functional groups.

EXAMPLE 1

Preparation of isosorbide di(methyl carbonate) According to the Invention 43 g of isosorbide (0.29 mol), then 1069 g of dimethyl carbonate (=40 molar equivalents, with respect to the isosorbide) and 123 g of potassium carbonate are introduced into a reactor with a capacity of 1.5 liters which is heated by a thermostatically controlled bath comprising a heat-exchange fluid and which is equipped with a paddle mechanical stirring system, with a system for controlling the temperature of the reaction medium and with a rectifying column surmounted by a reflux head. The reaction mixture is heated at total reflux for one hour, at the end of which time the temperature of the vapors at the column top reaches 64° C., before beginning the removal of the methanol formed. The heating of the reaction medium is subsequently maintained at a temperature of between 68° C. and 95° C. for 13 hours, at the end of which time the temperature of the vapors at the column top reaches 90° C. and stabilizes at this temperature (boiling point of dimethyl carbonate). This is the sign that the transesterification reaction is complete and that methanol is no longer being formed. The reaction medium is filtered in order to remove the suspended potassium carbonate therefrom. The clear and colorless solution comprises 95% of isosorbide di(methyl carbonate), 1% of isosorbide mono(methyl carbonate) and 4% of oligomers. It is devoid of unreacted isosorbide. The percentages correspond to area distributions by gas chromatographic analysis (the solvent, in this instance the dialkyl carbonate, being excluded).

EXAMPLE 2

Preparation of isosorbide di(methyl carbonate) According to the Invention

Example 1 is repeated with the only difference that not 40 equivalents but only 20 equivalents of dimethyl carbonate are used. The composition of the reaction medium obtained after removal of the catalyst particles is presented in table 1 below.

EXAMPLE 3

Preparation of isosorbide di(methyl carbonate) According to the Invention

Example 1 is repeated with the only difference that not 40 equivalents but only 10 equivalents of dimethyl carbonate are used. The composition of the reaction medium obtained after removal of the catalyst particles is presented in table 1 below.

EXAMPLE 4

Preparation of isosorbide di(ethyl carbonate) According to the Invention 25 g of isosorbide (0.17 mol), then 826 g of diethyl carbonate (=40 molar equivalents with respect to the isosorbide) and 70 g of potassium carbonate are introduced into a reactor identical to that used in example 1. The reaction mixture is heated at total reflux for one hour, before beginning the removal of the ethanol formed. Heating of the reaction medium is subsequently maintained at a temperature of 126° C. for 3 hours, at the end of which time the temperature of the vapors at the column top reaches 126° C. (boiling point of diethyl carbonate). This is the sign that the transesterification reaction is complete and that ethanol is no longer being formed. The reaction medium is filtered in order to remove the suspended potassium carbonate therefrom. The solution obtained, which is clear and colorless, comprises 96.6% of isosorbide di(ethyl carbonate), 0.3% of isosorbide mono(ethyl carbonate) and 3.1% of oligomers. It is devoid of unreacted isosorbide. The percentages correspond to area distributions by gas chromatographic analysis (the solvent, in this instance diethyl carbonate, being excluded).

EXAMPLE 5

Preparation of isosorbide di(ethyl carbonate) According to the Invention

Example 4 is repeated with the only difference that not 40 equivalents but only 10 equivalents of diethyl carbonate are used. The composition of the reaction medium obtained after removal of the catalyst particles is presented in table 1 below.

TABLE 1

| Ex. | Dialkyl carbonate | Dialkyl carbonate/ isosorbide | Iso- sorbide | Isosorbide mono(alkyl carbonate) | Isosorbide di(alkyl carbonate) | Oligo- mers |
|---|---|---|---|---|---|---|
| 1 | DMC | 40 | 0% | 1% | 95% | 4% |
| 2 | DMC | 20 | 0% | 3% | 85% | 11% |
| 3 | DMC | 10 | 0% | 2% | 80% | 18% |
| 4 | DEC | 40 | 0% | 1% | 95% | 4% |
| 5 | DEC | 10 | 0% | 8% | 75% | 17% |

These results show that the process according to the invention makes it possible to obtain, with virtually quantitative yields, isosorbide di(methyl carbonate) and isosorbide di(ethyl carbonate). The use of a large stoichiometric excess of dialkyl carbonate makes it possible to obtain products comprising approximately 95% by weight of the difunctional derivative.

A lower stoichiometric excess (10 equivalents) admittedly results in not insignificant fractions of oligocarbonates but the latter can be easily separated from the isosorbide di(alkyl carbonate)s by crystallization or distillation.

EXAMPLE 6

Preparation of isosorbide di(methyl carbonate) According to the Invention 430 g of isosorbide (0.29 mol), then 10.602 kg of dimethyl carbonate (=40 molar equivalents with respect to the isosorbide) and 1220 g of potassium carbonate are introduced into a reactor with a capacity of 20 liters with is heated by a thermostatically controlled bath comprising a heat-exchange fluid and which is equipped with a paddle mechanical stirring system, with a system for controlling the temperature of the reaction medium and with a rectifying column surmounted by a reflux head.

The reaction mixture is heated at a temperature of approximately 90° C. while continuously removing the methanol formed. After 5 hours, the temperature of the vapors at the column top reaches 90° C. and stabilizes at this temperature (boiling point of the dimethyl carbonate). This is the sign that the transesterification reaction is complete and that methanol is no longer being formed. The reaction medium is filtered in order to remove the suspended potassium carbonate therefrom. The clear and colorless solution comprises 95.9% of isosorbide di(methyl carbonate), 0.1% of isosorbide mono (methyl carbonate) and 4% of oligomers.

It is devoid of unreacted isosorbide. The percentages correspond to area distributions by gas chromatographic analysis (the solvent being excluded).

EXAMPLE 7

Purification of the isosorbide di(methyl carbonate) Obtained According to the Invention After evaporation of the unreacted dimethyl carbonate, 645 g of the product obtained according to example 6 are distilled under high vacuum (<1 mbar) on a wiped-film evaporator in short-path configuration. The jacket of the evaporator is heated to 160° C. and the internal condenser is maintained at a temperature of approximately 80° C. The product is introduced at 70° C. with a flow rate of 180 g/h.

The following are obtained:
a distillate in the form of a white solid comprising more than 99% by weight of isosorbide di(methyl carbonate) and comprising no trace of oligomers; and
a distillation residue comprising 95% by weight of oligomers.

EXAMPLE 8

Reversibility of the Transesterification Reaction According to the Invention 6.8 g of the oligomers corresponding to the residue obtained according to example 7 are introduced into a 250 ml three-necked round-bottomed flask equipped with a magnetic stirrer, heated by an electric mantle and surmounted by a reflux condenser. 173 g of dimethyl carbonate, 19.6 g of potassium carbonate and 3.2 g of methanol are subsequently introduced into said three-necked round-bottomed flask. The reaction medium is maintained at reflux at a temperature of 90° C. for 3 h. After filtering off the potassium carbonate, a clear and colorless solution comprising 14% of isosorbide di(methyl carbonate), 51% of isosorbide mono(methyl carbonate), 34% of isosorbide and 1% of oligomers is obtained. These percentages result from an area distribution gas chromatography analysis (the solvent, in this instance diethyl carbonate, being excluded).

EXAMPLE 9

Study of the Specificity of the Transesterification Catalyst

In order to evaluate the specificity of the catalyst in the transesterification reaction according to the invention, example 6 is repeated with the only difference that the catalyst is varied as follows: use is made either of 3 equivalents of potassium carbonate as in example 1, or of 3 equivalents of potassium hydroxide or of lithium hydroxide, or of hydrotalcite in an amount (weight for weight) equivalent to the amount of isosorbide. The hydrotalcite used is precalcined at 500° C. overnight. It is either the hydrotalcite Sorbacid® 911 or Sorbacid® 944, both sold by Süd-Chemie.

After evaporation of the dimethyl carbonate, the percentages (as area distribution) of isosorbide di(methyl carbonate) (iso DMC), isosorbide mono(methyl carbonate) (iso MMC), isosorbide, oligomers, dimethyl isosorbide (DMI), monomethyl isosorbide (MMI) and methyl isosorbide methyl carbonate (MI-MC) are determined by area distribution gas chromatography (the solvent, in this instance diethyl carbonate, being excluded).

| Catalyst | iso DMC | iso MMC | Iso-sorbide | Oligo-mers | DMI | MMI | MI-MC |
|---|---|---|---|---|---|---|---|
| LiOH | 95.0 | 0.6 | 0.1 | 4.3 | 0.0 | 0.0 | 0.0 |
| KOH | 83.0 | 12.0 | 0.0 | 5.0 | 0.0 | 0.0 | 0.0 |
| K$_2$CO$_3$ | 96.0 | 0.1 | 0.0 | 3.9 | 0.0 | 0.0 | 0.0 |
| Sorbacid ® 911 | 61.4 | 0.7 | 0.0 | 3.0 | 3.3 | 0.0 | 31.6 |
| Sorbacid ® 944 | 73.9 | 2.5 | 0.1 | 8.8 | 0.6 | 0.2 | 13.9 |

In contrast to hydrotalcites, potassium carbonate, potassium hydroxide and lithium hydroxide are specific catalysts for the transesterification reaction according to the invention.

EXAMPLE 10

Use of the Compounds According to the Invention in the Preparation of a Polymer

An amount of 50.6 g (0.19 mol) of isosorbide di(methyl carbonate) obtained according to example 6, 12.3 g (0.20 mol) of ethylene glycol and 0.2773 g (8.5×10$^{-4}$ mol) of cesium carbonate are introduced into a reactor with a capacity of 100 ml which is heated by a thermostatically controlled bath comprising a heat-exchange fluid and which is equipped with a paddle mechanical stirring system, with a system for controlling the temperature of the reaction medium, with a pipe for introducing nitrogen, with a distillation head connected to a condenser and to a receiver for collecting the condensates, and with a system for placing under vacuum with regulation. The assembly is placed under a nitrogen stream of 25 l/h and the reaction medium is heated by the heat-exchange fluid. The temperature is gradually raised while undergoing stationary phases of 30 min at 115° C., 140° C. and 165° C. The rise in temperature between each stationary phase is performed in 30 minutes. During the reaction, distillation of the methanol is observed. At the end of the stationary phase of 165° C., the assembly is placed under vacuum for 1 h 30 min (residual pressure of 3 mbar) in order to continue the distillation and while maintaining the temperature of 165° C. After cooling the reaction medium, a viscous polymer is obtained.

What is claimed is:
1. A process for the preparation of dianhydrohexitol di(alkyl carbonate) of formula (I)

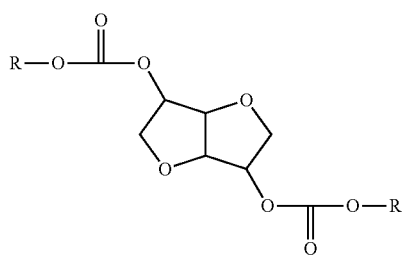

wherein each R independently represents a linear or branched alkyl group, said process comprising, in sequence, the following steps:
(a) preparing a starting reaction mixture comprising
at least one dianhydrohexitol,
at least 2 molar equivalents, with respect to the amount of dianhydrohexitol present, of at least one dialkyl carbonate of formula R—O—C(=O)—O—R, wherein R independently represents a linear or branched alkyl group, and
a transesterification catalyst,
(b) heating the reaction mixture up to a temperature of greater than or equal to the boiling point of an alcohol R—OH formed by the transesterification reaction, or greater than or equal to the boiling point of an azeotropic mixture which the alcohol R—OH forms with another component present in the reaction mixture, and at most equal to the boiling point of the reaction mixture, in a reactor equipped with a rectification column comprising a number of theoretical distillation plates sufficient to separate, from the reaction mixture, the alcohol R—OH or the azeotrope.

2. The process as claimed in claim 1, wherein the starting reaction mixture comprises from 2.1 to 100 molar equivalents of dialkyl carbonate, with respect to the amount of dianhydrohexitol initially present in the reaction medium.

3. The process as claimed in claim 1, wherein the transesterification catalyst is selected from:
acid catalysts,
alkali metal and alkaline earth metal carbonates and hydrogenocarbonates,
alkali metal and alkaline earth metal hydroxides,
alkali metal and alkaline earth metal phosphates, hydrogenophosphates and dihydrogenophosphates,
ammonium salts of ammonium carbonates, hydrogenocarbonates, hydroxides, phosphates, hydrogenophosphates or dihydrogenophosphates, and
amines.

4. The process as claimed in claim 1, wherein the transesterification catalyst is selected from sulfuric acid, para-toluenesulfonic acid, phosphoric acid, potassium carbonate, sodium carbonate, barium carbonate, cesium carbonate, potassium hydrogenocarbonate, sodium hydrogenocarbonate, lithium hydroxide, potassium hydroxide, sodium hydroxide, calcium hydroxide, hydrotalcites, sodium phosphate, potassium phosphate, pyridine, triethylamine and diisopropylamine.

5. The process as claimed in claim 1, wherein the transesterification catalyst is selected from potassium carbonate, potassium hydroxide and lithium hydroxide.

6. The process as claimed in claim 1, wherein the starting reaction mixture prepared in step (a) comprises from 0.1 to 10 molar equivalents of transesterification catalyst, with respect to the amount of dianhydrohexitol.

7. The process as claimed in claim 1, wherein the process additionally comprises monitoring the progression of the reaction.

8. The process as claimed in claim 1, wherein the heating in step (b) is continued up to a degree of progression of the reaction at least equal to 95%, the degree of progression of the reaction being defined by the following formula:

$$\text{Degree of progression (in \%)} = \frac{(Ni - Nt)}{Ni} \times 100$$

where
Nt=number of dianhydrohexitol hydroxyl functional groups remaining in the reaction medium at time t, and
Ni=initial number of dianhydrohexitol hydroxyl functional groups.

9. The process as claimed in claim 1, wherein the process additionally comprises at least one step of separating the dianhydrohexitol di(alkyl carbonate) obtained from a portion or all of the other components of the reaction mixture.

10. The process as claimed in claim 1, wherein the dianhydrohexitol is isosorbide.

11. The process as claimed in claim 1, wherein the dialkyl carbonate is diethyl carbonate.

12. The process as claimed in claim 1, wherein the process additionally comprises a step (c) of concentrating the dianhydrohexitol di(alkyl carbonate)(s) obtained in step (b) by evaporation of the dialkyl carbonate which has not reacted during said step (b).

13. The process as claimed in claim 12, wherein the process additionally comprises a step (d) of purifying the dianhydrohexitol di(alkyl carbonate)(s) concentrated in step (c).

14. The process as claimed in claim 13, wherein that a residue resulting from the purifying step (d) is recycled to the reaction mixture of step (a).

15. A compound selected from the group consisting of dianhydrohexitol di(ethyl carbonate), isoidide di(methyl carbonate) and isomannide di(methyl carbonate).

16. The compound as claimed in claim 15 wherein the dianhydrohexitol di(ethyl carbonate) is isosorbide di(ethyl carbonate).

17. A method of preparation of polycarbonates, polycarbamates or polythiocarbonates, comprising a polymerization step using at least one of the compounds obtained by the process as claimed in claim 1 as monomer or comonomer.

18. A method of extending, bridging, grafting or crosslinking a polymer carrying hydroxyl, amine, thiol, ester or oxazoline functional groups, using at least one of the compounds obtained by the process as claimed in claim 1 as chain-extending agent, bridging agent, grafting agent or crosslinking agent.

19. The process as claimed in claim 1, wherein each R independently represents a methyl or ethyl group.

20. The process as claimed in claim 1, wherein the starting reaction mixture prepared in step (a) comprises from 1 to 5 molar equivalents of transesterification catalyst, with respect to the amount of dianhydrohexitol.

* * * * *